US010342447B2

(12) United States Patent
Banerjee et al.

(10) Patent No.: US 10,342,447 B2
(45) Date of Patent: Jul. 9, 2019

(54) SYSTEMS AND METHODS FOR MODEL-BASED NON-CONTACT PHYSIOLOGICAL DATA ACQUISITION

(71) Applicant: ARIZONA BOARD OF REGENTS ON BEHALF OF ARIZONA STATE UNIVERSITY, Scottsdale, AZ (US)

(72) Inventors: Ayan Banerjee, Tempe, AZ (US); Sandeep K. S. Gupta, Phoenix, AZ (US); Priyanka Bagade, Hillsboro, OR (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/475,634

(22) Filed: Mar. 31, 2017

(65) Prior Publication Data

US 2017/0202474 A1 Jul. 20, 2017

Related U.S. Application Data

(60) Division of application No. 14/542,172, filed on Nov. 14, 2014, now Pat. No. 9,642,543, which is a
(Continued)

(51) Int. Cl.
*A61B 5/0456* (2006.01)
*A61B 5/024* (2006.01)
(Continued)

(52) U.S. Cl.
CPC .......... *A61B 5/0456* (2013.01); *A61B 5/0006* (2013.01); *A61B 5/0024* (2013.01);
(Continued)

(58) Field of Classification Search
CPC . A61B 5/0452; A61B 5/0402; A61B 5/04012; A61B 5/02438; A61B 5/0006;
(Continued)

(56) References Cited

U.S. PATENT DOCUMENTS 7,778,700 B2 * 8/2010 Park .................. A61B 5/7264
600/544
2009/0124869 A1 * 5/2009 Hu ..................... A61B 5/0432
600/301
(Continued)

*Primary Examiner* — Michael W Kahelin
*Assistant Examiner* — Minh Duc G Pham
(74) *Attorney, Agent, or Firm* — Yakov S. Sidorin; Quarles & Brady LLP

(57) ABSTRACT

System and method for non-contact acquisition of current physiological data representing a subject. A first electromagnetic wave representing current physiological status of a first subject is modified by a second electromagnetic wave representing current physiological status of a second subject in proximity to the first subject. A parameter of the first electromagnetic wave representing a first physiological status of a first subject is measured with electronic circuitry to extract a parameter of the second electromagnetic wave. Historical physiological data associated with the second subject is acquired. The current physiological data representing current physiological status of the second subject is then derived based on historical physiological data of the second subject and a comparison between the first and second parameters.

11 Claims, 5 Drawing Sheets

Related U.S. Application Data continuation-in-part of application No. 13/901,442, filed on May 23, 2013, now abandoned.

(60) Provisional application No. 61/904,572, filed on Nov. 15, 2013.

(51) Int. Cl.
| | |
|---|---|
| *A61B 5/00* | (2006.01) |
| *A61B 5/0452* | (2006.01) |
| *A61B 5/0205* | (2006.01) |
| *A61B 5/04* | (2006.01) |
| *A61B 5/0476* | (2006.01) |
| *A61B 5/0245* | (2006.01) |

(52) U.S. Cl.
CPC ........ *A61B 5/0205* (2013.01); *A61B 5/02405* (2013.01); *A61B 5/04014* (2013.01); *A61B 5/0452* (2013.01); *A61B 5/0476* (2013.01); *A61B 5/726* (2013.01); *A61B 5/7257* (2013.01); *A61B 5/0245* (2013.01)

(58) Field of Classification Search
CPC . A61B 5/0245; A61B 5/02405; A61B 5/0022; A61B 5/024
USPC .......................................... 600/301
See application file for complete search history.

(56) References Cited

U.S. PATENT DOCUMENTS

| | | | |
|---|---|---|---|
| 2012/0265080 A1* | 10/2012 | Yu ............................ | A61B 5/04 600/484 |
| 2014/0266696 A1* | 9/2014 | Addison .............. | A61B 5/1171 340/539.12 |

* cited by examiner

Algorithm 2 Algorithm for Extracting ECG from EEG using Wavelet Transform

1: Filter the EEG signal to remove DC offset.
2: Use Coiflet-1 wavelet to perform CWT on EEG signal.
3: Extract the scale 4 data from the CWT processed EEG signal.
4: Set window length to detect peaks in CWT processed EEG signal such that threshold y-values in the window length should represent R-peak.
5: Update window length after every 5 seconds by averaging the distance between R-peaks obtained in last 5 seconds.
6: Repeat step 5 to analyze the whole EEG signal by detecting all R-peaks in it.

FIG. 5

SYSTEMS AND METHODS FOR MODEL-BASED NON-CONTACT PHYSIOLOGICAL DATA ACQUISITION

CROSS-REFERENCE TO RELATED APPLICATIONS

The present application is a divisional from the U.S. patent application Ser. No. 14/542,172 filed on Nov. 14, 2014 and titled "Systems and Methods for Model-Based Non-Contact Physiological Data Acquisition" (now published as US 2015/0087931), which in turn claims priority from the U.S. Provisional Patent Application No. 61/904,572 filed on Nov. 15, 2013. U.S. patent application Ser. No. 14/542,172 is also a continuation-in-part of the U.S. patent application Ser. No. 13/901,442, filed on May 23, 2013, now abandoned. The disclosure of each of the above-referenced provisional patent applications is incorporated herein by reference.

STATEMENT REGARDING FEDERALLY SPONSORED RESEARCH

This invention was made with government support under CNS-0831544 and IIS-1116385 awarded by the National Science Foundation (NSF). The government has certain rights in the invention.

BACKGROUND

The present invention relates to systems and methods for acquiring physiological data. More particularly, the invention relates to a non-contact method for acquiring the current physiological data of a subject.

Electrocardiography is a methodology of recording of the electrical activity of the heart in a form of an electrocardiogram (ECG), which is a time-varying signal representing such activity. Electrocardiography is known to be an effective and non-invasive diagnostic tool for cardiac monitoring. Several systems have been developed for continuous, remote ECG-monitoring using Body Sensor Networks (BSNs), which include a wireless, battery-operated, body-worn sensor that collecting ECG data, and transmitting the data to a gateway device (such as a smart phone, for example). The gateway device reports these data over the internet to a remote base station, which is typically a hospital server or caregiver's computer. Such remote monitoring allows collecting the data during a person's regular daily activity and enables early detection of conditions such as tachycardia or angina. The availability of continuous long-term data can help identify gradual, long term trends in the cardiac health of at-risk patients.

While the physiological-signal-based approach eliminates the need for security key storage and complex exponentiation computation in sensors, the process of collection of physiological data with the use of a BSN on a human body is prone to security breaches and may jeopardize the privacy of the patient. A specific important concern is whether such security measures are vulnerable to attacks when the attacker is in close proximity to a BSN and senses physiological signals through non-contact processes such as, for example, electromagnetic coupling: when two individuals are in close proximity, the electrocardiographic signal of one person can couple with an electroencephalographic signal of the other.

The possibility of procuring physiological information about a person with non-contacting means begs a question of how obviate or patch such vulnerability, and defines a need in a secure system and method configured for acquisition of physiological data using a non-contact method and monitoring at least one subject with no sensors attached in a non-clinical setting where monitoring systems are conventionally not robust against security attacks.

SUMMARY

Solutions provided by the present invention overcome the aforementioned drawbacks by establishing a non-contact method for acquisition of current physiological data from a subject with no sensors attached to the subject.

In accordance with one embodiment of the invention, a method for non-contact acquisition of current physiological data representing a subject is disclosed. The method includes analyzing, with electronic circuitry, a first descriptor of a first electromagnetic wave representing a first physiological status of a first subject to extract a second descriptor of a second electromagnetic wave representing a second physiological status of a second subject, said first electromagnetic wave having been modified by the second electromagnetic wave. The method further includes acquiring a set of historical physiological data associated with the second subject. The current physiological data, associated with the second subject is derived based on the set of historical physiological data and a comparison between the first and second descriptors.

In accordance with another embodiment of the method of the invention, the method includes analyzing, with electronic circuitry, a first descriptor of an electroencephalogram (EEG) wave representing a first physiological status of a first subject to extract a second descriptor of an electrocardiogram (ECG) wave representing a second physiological status of a second subject, the EEG wave having been modified by the ECG wave. The method further includes acquiring a set of historical physiological data associated with the second subject. The current physiological data associated with the second subject is derived based on the set of historical physiological data and a comparison between the first and second descriptors.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The invention will be more fully understood by referring to the following Detailed Description in conjunction with the generally not-to scale Drawings, of which:

FIG. 5 is a chart showing an algorithm for extracting ECG data from EEG data using wavelet transform according to an embodiment of the present invention.

The sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

Wireless sensors in Body Sensor Networks (BSNs) typically employ some form of cryptography to encrypt physiological data while sending it to a base station over the insecure wireless channel. The use of physiological data, collected by the sensors to generate cryptographic keys was proposed to be used for secure communication as a lightweight and usable alternative to traditional elliptic key or shared secret key cryptography. Physiological-signal-based security has two working principles: a) time variance: the features used for generation of cryptographic keys vary over time and hence replay intrusions are not possible, and b) variance among individuals, where physiological features of one individual is very different from those of the other. Hence, an implicit assumption is that to break the physiological signal based security the attacker has to possess the sample by sample physiological data, which was used to generate the key.

In fact, these two assumptions may not hold and physiological-signal-based security can be perturbed using generative models, which only require certain limited features (such as data acquired in the past, as opposed to sample-by-sample physiological measurements) to be operable.

Generative models are developed to regenerate physiological signals by using morphology and signal variations from historical or raw data (past data). These models are trained using the historical or raw data so that they can replicate the diagnostic features for a particular person. Generative models use clinically important features from physiological signals such as R-R interval, high frequency and low frequency ratio, and heart rate for ECG signal. The signal obtained from sensor and synthetic signal obtained from generative model are not time synchronized. In other words, the existing generative models provide signals (data) that are equivalent, in some key parameters, to the present, current physiological signals and parameters characterizing the subject at this moment.

However, the signals of the generative models are well correlated in frequency domain because of the same diagnostic features. Currently available BSN security methods rely on diagnostic features of human physiology. Generative models also use these features to generate physiological signals which do not vary over time.

If a generative model of the physiological signal using past data is available, then, based on such signal, diagnostically-equivalent present signals can be regenerated and used to gain understanding of the current status of the subject.

Figure 1:
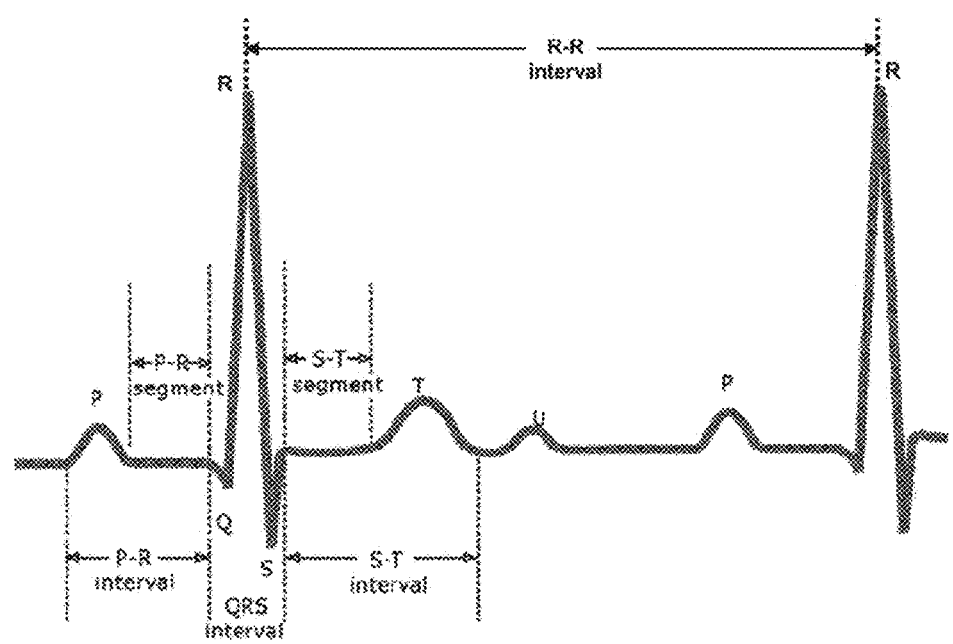
FIG. 1 is a diagram of an ECG beat.

The ECG signal has been extensively studied and used for cardiac diagnosis. The basic unit of an ECG is a so-called "beat" signal, and the shape of this beat signal is referred to as the ECG morphology. Referring to FIG. 1 (showing a single beat and a portion of the following beat), a single beat includes P, Q, R, S and T waves, with a U wave present in some cases. The R wave is typically the most prominent and easy to identify in a beat. The Q, R and S waves are often jointly considered in a single complex, called the QRS complex. The shape, amplitude and relative locations of the constituent waves are key features of an ECG, and are referred to herein as morphology features. These features vary across individuals, but are expected to remain fairly stable for a given person, in the absence of pathological conditions.

The duration of time between two consecutive R peaks is referred to the R-R interval, and a value reciprocal to this duration of time provides the instantaneous heart rate. Even in a healthy person, the R-R interval varies across beats due to several physiological factors. This variation is described using temporal features such as mean and standard deviation of heart rate, for example, and spectral features such as Low Frequency/High Frequency (LF/HF) ratio. The temporal and spectral features of the ECG are referred to herein as inter beat features.

An ECG is inherently a low amplitude electrical signal and is often corrupted by noise from various sources such as those associated with equipment (for example, electrical mains), muscle, and patient movement or respiration. As a result, the measured signal must be filtered to extract the underlying ECG waveform. Among the constituent waves, the QRS complex of a beat can be determined using computationally lightweight, not consuming substantial computational time algorithms. The extraction of data representing P and T waves, however, requires advanced filtering techniques that are computationally expensive to implement on sensors.

In contradistinction with the related art, embodiments of the present invention utilize a generative ECG model configured to produce synthetic (created by a user based on computational models, in reliance on limited information) ECG signals based on a set of input parameters. Some embodiments of the invention may use one of or a combination of known dynamic model generators, such as ECGSYN. ECGSYN provides modeling of an ECG signal as a point moving around a unit circle, and employs differential equations to describe its motion. See, for example, www.physionet.org/physiotools/ecgsyn. The individual waves are modeled as a summation of Gaussian functions.

Embodiments of the present invention, providing a novel generative-model-based technique to acquire physiological data, is based on the realization that, caused by the electromagnetic filed generated by the human heart, the ECG signal of one subject and the EEG signal of another subject that are in close proximity to one another, may be operably coupled. Using this coupling principle, an embodiment of the present invention allows the first subject to non-invasively obtain the physiological data of the second subject without requiring the second subject to wear any devices on his body. In addition, the physiological data of the second subject may be acquired without the first subject being in contact with the second subject.

The inter-beat features of ECG are modeled, according to ECGSYN, using 3 parameters: hrmean, hrstd and lfhfratio, corresponding to mean heart rate, standard deviation of heart rate and LF/HF ratio respectively. For the morphology features, each wave is represented by 3 parameters: (a, b, θ), which determine its height, width and distance to R peak, respectively. For example, the Q wave is represented by the 3-tuple ($a_Q$, $b_Q$, and $\theta_Q$).

Figure 2:
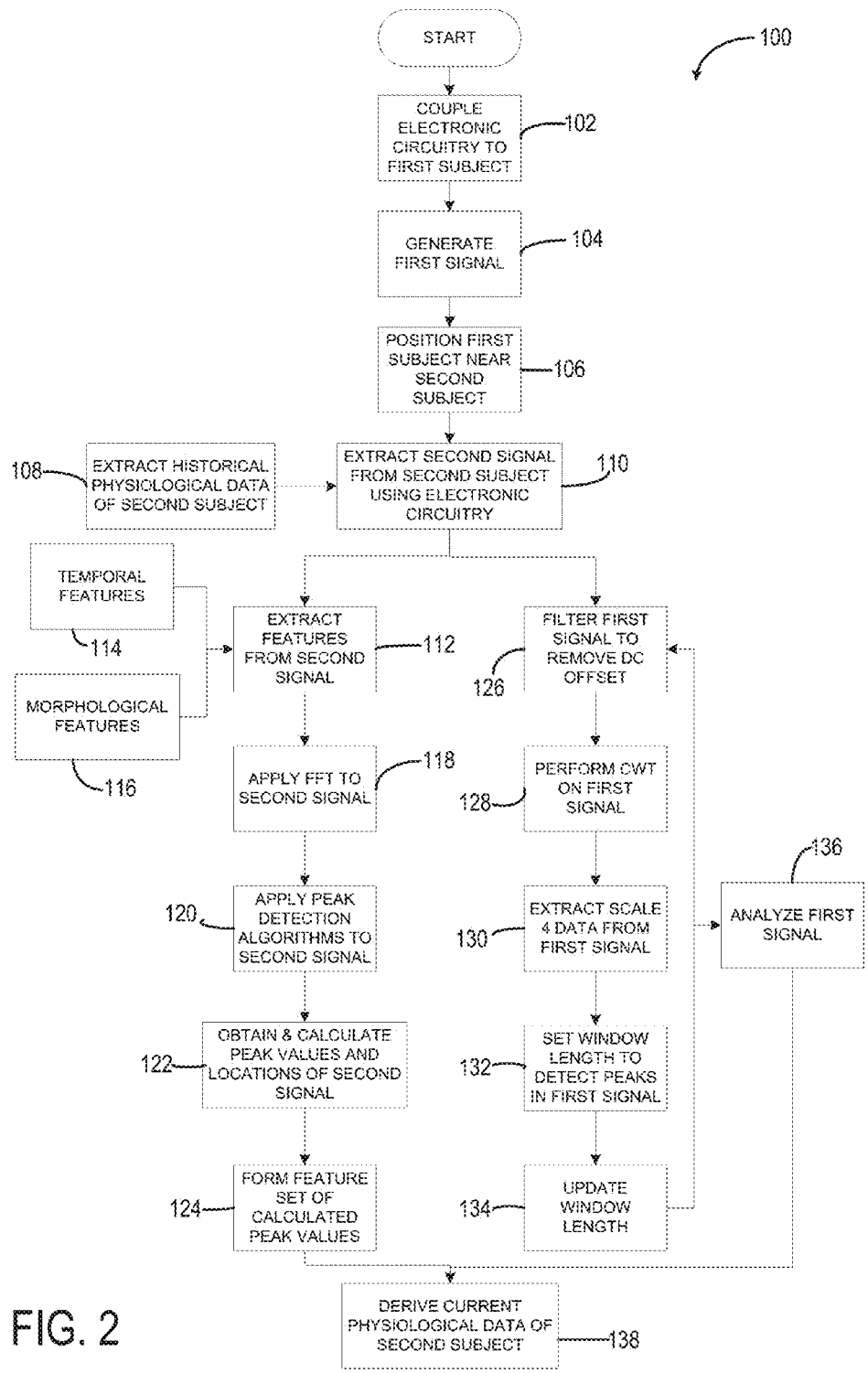
FIG. 2 is a flow chart setting forth the steps of processes for acquiring physiological data from a subject in accordance with an embodiment.

Referring now to FIG. 2, a flow chart 100 (showing some steps of a method for non-contact acquisition of current physiological data representing a subject) is provided. To start the data acquisition process, a first subject (for example, a caregiver) may be equipped with electronic circuitry at process block 102. Such electronic circuitry may include a lead, a sensor or another device appropriately configured to detect an electromagnetic signal (such as, for example, an EEG signal). The first subject may be a human or even non-human (provided that such non-human subject is chosen to produce a measureable electromagnetic signal at process block 104). The electronic circuitry may be worn by the first subject or otherwise coupled to the first subject so that the EEG signal of the first subject may still be measured by the electronic circuitry. For example, in one embodiment, the electronic circuitry may be coupled to the first subject's head or to another portion of the first subject's body, such as their chest or arm. Alternatively, the electronic circuitry may be wirelessly coupled to the first subject.

At process step 106, a second subject (the target subject, whose current physiological data are to be collected, for example a patient under the care of the firs subject) and the first subject equipped with the electronic circuitry are positioned in close proximity to each other. In an alternative embodiment, the first and second subject may be in physical contact with each other. Such physical contact, however, is not generally required.

At process block 108, a set of historical (reference) physiological data of the second subject (that may have been previously acquired and stored on appropriate tangible, non-transitory storage medium) is obtained (extracted) from the storage. The set of historical physiological data may be processed with a data processor (not shown) configured to access the tangible storage medium. The electronic circuitry may then acquire an ECG signal from the second subject at process block 110. The electronic circuitry may also define a plurality of features from the data representing the ECG signal at process block 112. A methodology of defining such features of the ECG signal may be performed as described in the U.S. patent application Ser. No. 13/901,442, the disclosure of Which is incorporated by reference herein in its entirety.

As described above, the generative algorithm may be a function of time and physiological parameters of the ECG signal, $G=f(t, a, b, c, \ldots)$. The parameters a, b, c, and so on can be of two types as shown at process blocks 114 and 116, respectively: (1) temporal parameters, which represent time properties of the signal (such as, for example, average heart rate, standard deviation) and (2) morphological parameters, which represent the shape of the signal (e.g., relative height of R peak with respect to Q peak for ECG signals). The temporal features at process block 114 are often used for diagnosis while the morphological parameters at process block 116 are obtained through a training phase. In the training phase, an interval of the physiological signal is taken and a mathematical model is fitted to it. The parameters of the mathematical model capture the morphology of the signal.

The ECG signal has five peaks: P, Q, R, S. and T. Each peak may be represented using a Gaussian function with parameters a, b, and $\theta$ which determine its height, width, and distance to R peak, respectively. The inter-beat features of ECG (i.e., mean and standard deviation of heart rate and LF/HF ratio) may be modeled using three parameters: hrmean, hrstd and lfhfratio, respectively.

The ECG signal may be processed in a frequency domain which may give a better idea about the physiology of the second subject as compared to time domain. In the feature extraction process at process block 112, a FFT algorithm may be applied to the ECG signal at process block 118. Afterwards, at process block 120 a peak detection algorithm may be applied on the processed ECG signal to get peak values $p_v$ and the locations of the peaks $p_i$, as shown at process block 122. For every peak, the feature is calculated as concatenation of location of peak and its value, $p_v p_i$. The set of all calculated features for every peak in the FFT processed signal forms an extracted feature set for that signal at process block 124. This set of calculation may be done for each sensor in the network. Because the physiological signals, such as the ECG signal, do not change in their morphology over time, historical physiological data of the second subject may be used to learn the morphological features of the generative models. However, to obtain temporal features, the concept recognized as a principle of electricity of touch (according to which an exchange of electromagnetic energy produced by the heart is defined and occurs when people touch or are in proximity of one another) may be used. The electromagnetic field generated by heart is much stronger than that of brain electrical signals. It has been experimentally proven that, due to the stronger electromagnetic field generated by heart, whenever people come in contact with each other or even if they are in proximity with each other, the heart signal of one person gets reflected in the brain signal of other person, as shown at process block 110. If ECG and EEG for different people in contact by touch or in proximity are overlayed then they show similar wave form. Also, particularly the alpha wave in the EEG signal of one person has a strong relation with R-waves in the ECG signal of other person in close proximity. Using this result, the electronic circuitry of the first subject may have access to temporal features by only holding hands or staying in proximity with that person while wearing the electronic circuitry (e.g., an EEG sensor).

Figure 3:
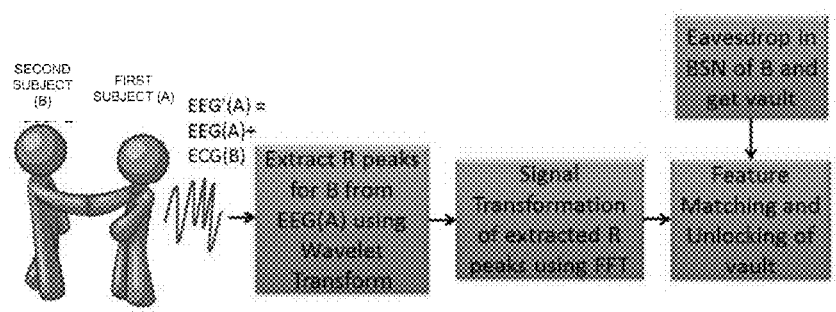
FIG. 3 is a diagram illustrating schematically one implementation of the process illustrated in FIG. 2.
Figure 4:
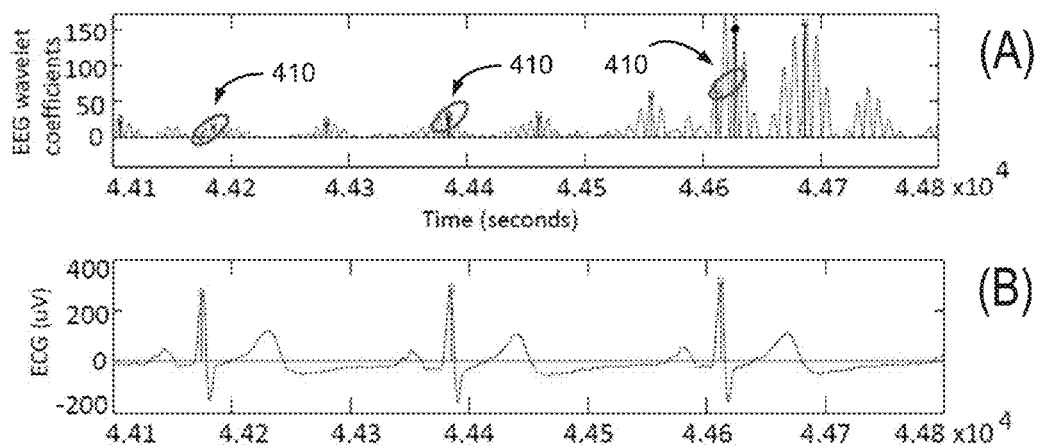
FIGS. 4A and 4B are graphs showing, respectively, R peaks from ECG data and a wavelet transform of EEG data in accordance with an embodiment.

FIG. 3 schematically illustrates steps of acquisition of the features of the ECG signal from the second subject using the electronic circuitry attached to the first subject. Such data acquisition turns on the idea that the EEG signal (and, in particular, alpha-wave) of one person has a strong relation to the R-waves in the ECG signal of another person with whom the other is in contact. Here, the first subject wears an EEG sensor, sensing EEG(A), and comes in close proximity of the second subject sensing ECG(B). The first subject ("intruder") comes in close proximity (or even in contact with by, for example, shaking hands) with example, with the second subject ("target") and his EEG, EEG'(A) that contains EEG(A) plus the ECG R waves of the second subject (ECG(B)). The first subject's electronic circuitry then appropriately samples the EEG signals to perform a windowed wavelet transform, as will be described in detail below, on EEG'(A). For each upward wave of ECG(B) there exists a corresponding "oscillation" in the wavelet transform. The oscillations are localized and converted to peaks using an adaptive thresholding technique. The R peaks from ECG(B) and the peaks of wavelet coefficients of EEG(A) are shown in FIGS. 4A, 4B. According to the idea of the invention, the data representing peaks obtained from EEG'(A) may then be used to determine the heart rate, standard deviation, and LF/HF ratio of ECG(B). The data processing involves removing the EEG peaks 410 corresponding to P, Q, S, and T waves in the ECG by performing peak detection in the ECG and appropriate mapping of such detected peaks to EEG peaks. The so determined temporal features combined with the morphology features can be used to generate the ECG signals of the target.

Referring again to FIG. 2, at process block 128 a continuous wavelet transform (CWT) may be performed on the EEG signal to capture temporal and morphological features in the signal to enable the CWT to be further used for analyzing physiological signals. A CWT provides information about the available frequencies in the signal at a particular time, whereas the Fourier transform (FT) can only illustrate frequency content in the overall signal. Therefore, to identify ECG signals within the EEG signal, a CWT is preferred over the FT as both temporal and morphological information are required. CWT uses a basic signal function which is scaled according to the frequency and time shift allowing specific shape properties of the signal to be analyzed. CWT for x(t) may be expressed as shown in Formula (1) below:

$$x(t) = \frac{1}{\sqrt{a}} \int_{-\infty}^{\infty} x(t) \varphi * \left( \frac{t-b}{a} \right) dt, \quad (1)$$

where, a>0 is a scaling parameter, b is a shift parameter and φ is a wavelet function. The scale parameter a may be used to denote how much the wavelet is stretched or compressed. Smaller values of a may suggest a more compressed wavelet, whereas larger values of a would indicate that the shape of the wavelet is more stretched. R-peaks in ECG from EEG signal are then obtained using Coiflet-1 wavelet with scale parameter 4 (see, for example, J.-A. Jiang et al., *Computers in biology and medicine*, vol. 37, no. 11, pp. 1660-1671, 2007; incorporated herein by reference) as shown at process block 130. Extraction of ECG R-peaks from the EEG with the use of the CWT can be effectuated with the use of an algorithm some steps of which are shown in FIG. 5. These R-peaks may be further used to create model for ECG signal of the second subject (target).

Notably, extracting the ECG signal of the second ("target") subject from the EEG signal of the first ("intruder") subject at process block 110 may be complemented with filtering the EEG signal of the first subject to remove a DC offset at process block 126. The wavelet transformations already performed may have the effect of enhancing the frequency of the EEG signal. (When the frequency of the EEG signal is enhanced, the embedded ECG signal also experienced amplification and its detection becomes simplified.) In one specific embodiment, the model may be only concerned with the frequency spectrum excluding a DC signal and therefore the DC offset may be removed from the calculations. Indeed, a signal practically qualified as a DC signal is a low-frequency signal, and typically corresponds to those frequencies at which the breathing activity occurs. The present invention is not concerned with breathing activity, so the DC-like signals are eliminated from consideration. Once the DC offset as has been removed at process block 126, a Coiflet-1 wavelet may be used to perform a continuous wavelet transform (CWT) on the EEG signal at process block 128, as previously mentioned.

The purpose of the Coiflet-1 wavelet is to isolate an ECG signal embedded within the EEG signal. This may be more easily accomplished using the Coiflet-1 wavelet because of its similarities to an ECG signal (as compared with, for example, haar or Mexican hat wavelets known in the art, which are deficient in resembling ECG signals). By repeatedly measuring the signal peak within a shifting timing window, the R-peak may be established for a given ECG signal. In other embodiments, detecting the ECG signal within the EEG signal is not limited to using the Coiflet wavelet. Other methods or wavelets may be used to accomplish the task of isolating the ECG signal within the EEG signal.

In further reference to FIGS. 2 and 5, after the EEG signal has undergone a Coiflet transformation (or another transformation as appropriate), the ECG signal may be extracted from the EEG signal using a scale 4 data, for example, at process block 130. The scale data allows the stretching or compressing of the ECG signal (transformed with the Coiflet) for the purposes of measuring the ECG signal. Such scaling of the Coiflet allows the wavelet to be shrunk or stretched to match the ECG signal. A window length may be set (a specific number of samples starting at a specific point and ending at another specific point) to detect a plurality of peaks in the Coiflet processed EEG signal at process block 132. The window length of the algorithm of FIG. 5 may be updated and/or adjusted at process block 134 and subjected to the steps previously outlined above. In an exemplary embodiment, the window length is adjusted at process block 134 every 5 seconds, however, this window-update period of time may be shorter or longer in other embodiments. At process block 136, the whole EEG signal is analyzed by detecting all R-peaks in it. By comparing the features of the EEG and ECG signals and the historical physiological data of the second subject, the current physiological data of the second subject may be derived at process block 138.

Figure 6:
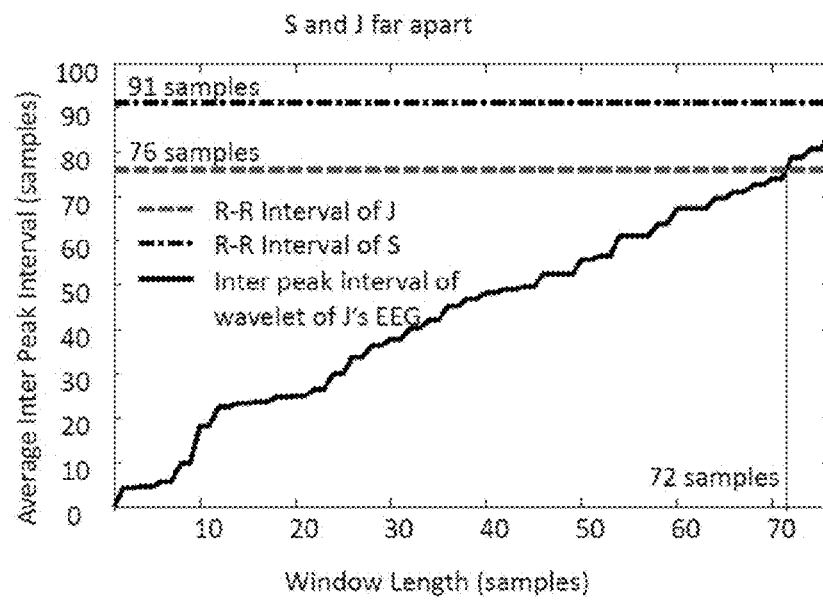
FIG. 6 is a graph showing a comparison of R-R intervals of a first and second subject that are far apart, and an average inter peak interval of a wavelet transform of the first subject's EEG.
Figure 7:
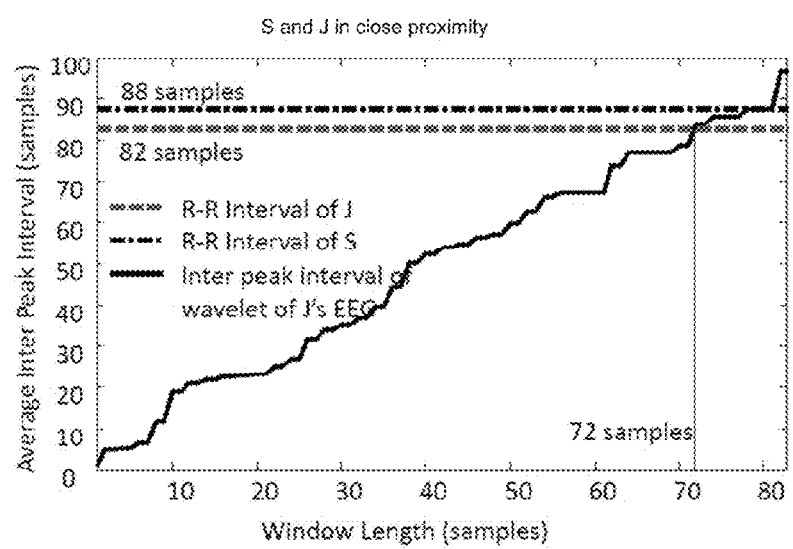
FIG. 7 is a graph showing a comparison of R-R intervals of the first and second subject of FIG. 6 that are in close proximity, and an average inter peak interval of a wavelet transform of the first subject's EEG.

Referring now to FIGS. 6 and 7, an example is provided of application of the Algorithm 2 of FIG. 5 to the first subject (J) and the second subject (S), initially in a first time period (corresponding to FIG. 6), the first and second subjects are spatially separated from one another. In a following second time period (corresponding to FIG. 7), the first and second subject are in close proximity of one another. Each of the first and second time periods was set to 30 seconds. The window length of Algorithm 2 was varied from 1 sample to 128 samples. The inter peak interval (between the peaks determined from EEG signals) was determined. When the first subject (J) was away from the second subject (S), the average inter peak interval of the wavelet of the first subject's EEG (with a window length equal to the average R-R interval of the first subject) was equal to the average R-R interval of the first subject. However, when the first and second subjects were in proximity, the average inter peak interval of the wavelet transform of the first subject's EEG (with a window length equal to the average R-R interval of the first subject's ECG) was reduced considerably thereby indicating an overlap of the second subject's and the first subject's R peaks in the first subject's ECG, as shown in FIG. 7. The R peaks of the second subject were then obtained by removing the first subject's R peaks from the peaks obtained from the first subject's EEG's wavelet transform. The minimum and maximum probabilities were 0.24 and 0.5, respectively. Accordingly, the current physiological data and diagnostic parameters of the second subject were determined based on the first subject's EEG.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, when the present disclosure describes features of the invention with reference to corresponding drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A skilled artisan will recognize that the invention may possibly be practiced without one or more of the specific features, elements, components, structures, details, or characteristics, or with the use of other methods, components, materials, and so forth. Furthermore, the described single features, structures, or characteristics of the invention may be combined in any suitable manner in one or more further embodiments.

The invention as recited in claims appended to this disclosure is intended to be assessed in light of the disclosure as a whole, including features disclosed in prior art to which reference is made.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for non-contact acquisition of current physiological data representing a subject, the method comprising:
    analyzing, with electronic circuitry, a first parameter of an electroencephalogram (EEG) wave representing a first physiological status of a first subject to extract a second parameter of an electrocardiogram (ECG) wave representing a second physiological status of a second subject,
    said EEG wave having been modified by the ECG wave;
    acquiring, from a tangible storage medium, a set of historical physiological data associated with the second subject;
    and
    deriving at least a mean heart rate, a standard deviation of heart rate, and a low-frequency-to-high-frequency ratio of heart rate of the second subject based on said set of historical physiological data and a comparison between the first and second parameters;
    producing a report identifying whether the second subject has tachycardia or angina based on said at least at least a mean heart rate, a standard deviation of heart rate, and a low-frequency-to-high-frequency ratio of heart rate.

2. The method of claim 1, further comprising attaching the electronic circuitry to the first subject, the electronic circuitry being at least one of a lead, a sensor, and a device configured to detect an EEG wave.

3. The method of claim 1, wherein said deriving comprises:
    performing, with a programmable processor, a fast fourier transform (FFT) of the ECG wave to generate a first signal;
    applying a peak detection algorithm to the first signal to obtain a plurality of peak values and temporal parameters of the first signal;
    calculating peak features for each of the plurality of peak values; and
    generating a feature set including the peak features for each of the plurality of peak values in the first signal.

4. The method of claim 1, wherein said deriving the current physiological data further comprises:
    a) filtering the EEG wave emitted by the first subject to remove a DC offset thereof;
    b) performing a continuous wavelet transform (CWT) of the EEG wave to form a CWT-transformed EEG wave;
    c) extracting a scale 4 data from the CWT-transformed EEG wave;
    d) setting a duration of a time-window to detect a plurality of peaks of said CWT-transformed EEG wave;
    e) updating a value of said duration; and
    f) repeating steps a) through e) to analyze said EEG wave.

5. The method of claim 4, wherein said performing a continuous wavelet transform (CWT) on the EEG wave employs a Coiflet-1 wavelet algorithm.

6. The method of claim 4, wherein the duration of a time-window is chosen to detect a threshold value to represent an R-peak of the ECG wave.

7. The method of claim 4, wherein said updating includes setting a time-window of a second duration every 5 seconds by averaging a distance between R-peaks of the ECG wave that have been determined during a time-window of a first duration, the time window of the first duration having been set prior to setting the time-window of the second duration.

8. The method of claim 1, wherein the first subject and the second are at least one of a human and a non-human.

9. The method of claim 1, further comprising positioning the first subject in close proximity to the second subject.

10. The method of claim 1, wherein said deriving the current physiological data associated with the second subject using a principle of electricity of touch.

11. The method of claim 1, further including analyzing the historical physiological data and comparing the first and second parameters with data analyzing circuitry to obtain the current physiological data representing the first subject.

* * * * *

UNITED STATES PATENT AND TRADEMARK OFFICE
CERTIFICATE OF CORRECTION

PATENT NO. : 10,342,447 B2
APPLICATION NO. : 15/475634
DATED : July 9, 2019
INVENTOR(S) : Ayan Banerjee, Sandeep K. S. Gupta and Priyanka Bagade It is certified that error appears in the above-identified patent and that said Letters Patent is hereby corrected as shown below:

In the Specification

Column 1, Line 24:
Please delete the following paragraph:
"This invention was made with government support under CNS-0831544 and IIS-1116385 awarded by the National Science Foundation (NSF). The government has certain rights in the invention."

And replace with the following paragraph:
-- This invention was made with government support under 0831544 and 1116385 awarded by the National Science Foundation. The government has certain rights in the invention. --

Signed and Sealed this
Seventeenth Day of March, 2020

Andrei Iancu
*Director of the United States Patent and Trademark Office*